(12) United States Patent
Erskine

(10) Patent No.: US 9,180,277 B2
(45) Date of Patent: Nov. 10, 2015

(54) RELEASE MECHANISM FOR USE WITH NEEDLE SHIELDING DEVICES

(75) Inventor: Timothy J. Erskine, Sister Bay, WI (US)

(73) Assignee: Erskine Medical LLC, High Falls, NY (US)

( * ) Notice: Subject to any disclaimer, the term of this patent is extended or adjusted under 35 U.S.C. 154(b) by 203 days.

(21) Appl. No.: 13/997,973

(22) PCT Filed: Dec. 2, 2011

(86) PCT No.: PCT/US2011/063118
§ 371 (c)(1),
(2), (4) Date: Jun. 25, 2013

(87) PCT Pub. No.: WO2012/075421
PCT Pub. Date: Jun. 7, 2012

(65) Prior Publication Data
US 2014/0046272 A1 Feb. 13, 2014

Related U.S. Application Data

(60) Provisional application No. 61/419,005, filed on Dec. 2, 2010.

(51) Int. Cl.
*A61M 5/00* (2006.01)
*A61M 25/06* (2006.01)
(Continued)

(52) U.S. Cl.
CPC ....... *A61M 25/0618* (2013.01); *A61M 25/0009* (2013.01); *A61M 5/3273* (2013.01); *A61M 2005/325* (2013.01); *Y10T 29/49826* (2015.01)

(58) Field of Classification Search
CPC ............... A61M 25/0009; A61M 25/0618; A61M 2005/325; A61M 5/3273; Y10T 29/49826

USPC ........................................................ 604/263
See application file for complete search history.

(56) References Cited

U.S. PATENT DOCUMENTS 2,798,487 A 7/1957 Ferguson
3,459,183 A 8/1969 Ring et al.
(Continued)

FOREIGN PATENT DOCUMENTS

CN 1145813 A 3/1997
CN 1547493 A 11/2004
(Continued)

OTHER PUBLICATIONS

Erskine, Australian IP Examination Report No. 2 dated Feb. 25, 2010, Reference No. 30355386/MRF/TLG/tzs, Application No. 2006220690, 2 pages.
(Continued)

*Primary Examiner* — Jason Flick
(74) *Attorney, Agent, or Firm* — Hoffman Warnick LLC

(57) ABSTRACT

A needle-based medical device and method of manufacturing the same are disclosed. A needle device includes a hub having a longitudinal axis; a needle having a sharp distal tip; and a needle shield assembly associated with the needle and moveable from a non-shielding position to a shielding position. In the shielding position, the sharp distal tip is covered by at least part of the needle shield assembly. A latch is further provided for engaging with the hub when the needle shield assembly is in the non-shielding position; as well as a locking member operably connected to the needle shield assembly, and located at least partially within the hub when the needle shield assembly is in the non-shielding position. The latch and locking member lock the latch to the hub, such that when the needle shield assembly moves into the shielding position, the locking member moves generally proximally, unlocking the latch.

26 Claims, 15 Drawing Sheets

(51) Int. Cl.
*A61M 25/00* (2006.01)
*A61M 5/32* (2006.01)

(56) References Cited

U.S. PATENT DOCUMENTS

| | | | |
|---|---|---|---|
| 4,588,398 A | 5/1986 | Daugherty et al. |
| 4,596,563 A | 6/1986 | Pande |
| 4,755,170 A | 7/1988 | Golden |
| 4,762,516 A | 8/1988 | Luther et al. |
| 4,778,453 A | 10/1988 | Lopez |
| 4,790,828 A | 12/1988 | Dombrowski et al. |
| 4,832,696 A | 5/1989 | Luther et al. |
| 4,834,718 A | 5/1989 | McDonald |
| 4,846,809 A | 7/1989 | Sims |
| 4,863,436 A | 9/1989 | Glick |
| 4,887,998 A | 12/1989 | Martin et al. |
| 4,927,414 A | 5/1990 | Kulli |
| 4,929,241 A | 5/1990 | Kulli |
| 4,931,048 A | 6/1990 | Lopez |
| 4,944,725 A | 7/1990 | McDonald |
| 4,952,207 A | 8/1990 | Lemieux |
| 4,978,344 A | 12/1990 | Dombrowski et al. |
| 5,049,136 A | 9/1991 | Johnson |
| 5,059,180 A | 10/1991 | McLees |
| 5,116,326 A | 5/1992 | Schmidt |
| 5,120,320 A | 6/1992 | Fayngold |
| 5,160,325 A | 11/1992 | Nichols et al. |
| 5,215,528 A | 6/1993 | Purdy et al. |
| RE34,416 E | 10/1993 | Lemieux |
| 5,261,895 A | 11/1993 | Kablik |
| 5,300,045 A | 4/1994 | Plassche, Jr. |
| 5,304,151 A | 4/1994 | Kuracina |
| 5,322,517 A | 6/1994 | Sircom et al. |
| 5,328,482 A | 7/1994 | Sircom et al. |
| 5,334,158 A | 8/1994 | McLees |
| 5,344,408 A | 9/1994 | Partika |
| 5,360,408 A | 11/1994 | Vaillancourt |
| 5,360,497 A | 11/1994 | Schneider et al. |
| 5,376,075 A | 12/1994 | Haughton et al. |
| 5,429,611 A | 7/1995 | Rait |
| 5,447,501 A | 9/1995 | Karlsson et al. |
| 5,458,658 A | 10/1995 | Sircom |
| 5,466,223 A | 11/1995 | Bressler et al. |
| 5,558,651 A | 9/1996 | Crawford et al. |
| 5,582,597 A | 12/1996 | Brimhall et al. |
| 5,584,809 A | 12/1996 | Gaba |
| 5,599,310 A | 2/1997 | Bogert |
| 5,601,536 A | 2/1997 | Crawford et al. |
| 5,611,781 A | 3/1997 | Sircom et al. |
| 5,662,610 A | 9/1997 | Sircom |
| 5,669,927 A | 9/1997 | Boebel et al. |
| 5,683,365 A | 11/1997 | Brown et al. |
| 5,690,619 A | 11/1997 | Erskine |
| 5,697,907 A | 12/1997 | Gaba |
| 5,700,250 A | 12/1997 | Erskine |
| 5,718,688 A | 2/1998 | Wozencroft |
| 5,755,699 A | 5/1998 | Blecher et al. |
| 5,795,339 A | 8/1998 | Erskine |
| 5,853,393 A | 12/1998 | Bogert |
| 5,879,337 A | 3/1999 | Kuracina et al. |
| 5,951,515 A | 9/1999 | Osterlind |
| 5,951,525 A | 9/1999 | Thorne et al. |
| 6,001,080 A | 12/1999 | Kuracina et al. |
| 6,004,294 A | 12/1999 | Brimhall et al. |
| 6,117,108 A | 9/2000 | Woehr et al. |
| 6,210,371 B1 | 4/2001 | Shaw |
| 6,221,047 B1 | 4/2001 | Greene et al. |
| 6,379,333 B1 | 4/2002 | Brimhall et al. |
| 6,443,929 B1 | 9/2002 | Kuracina |
| 6,595,955 B2 | 7/2003 | Ferguson et al. |
| 6,629,959 B2 | 10/2003 | Kuracina et al. |
| 6,659,984 B2 | 12/2003 | Crawford et al. |
| 6,689,102 B2 | 2/2004 | Greene |
| 6,695,814 B2 | 2/2004 | Greene et al. |
| 6,743,186 B2 | 6/2004 | Crawford et al. |
| 6,749,588 B1 * | 6/2004 | Howell et al. ............ 604/164.08 |
| 6,761,706 B2 | 7/2004 | Vaillancourt |
| 6,786,891 B2 | 9/2004 | Hiejima |
| 6,860,871 B2 | 3/2005 | Kuracina et al. |
| 6,881,202 B2 | 4/2005 | Coleman et al. |
| 6,976,976 B2 | 12/2005 | Doyle |
| RE38,996 E | 2/2006 | Crawford et al. |
| 6,997,902 B2 | 2/2006 | Thorne et al. |
| 7,125,397 B2 | 10/2006 | Woehr et al. |
| 7,144,387 B2 | 12/2006 | Millerd |
| 7,264,613 B2 | 9/2007 | Woehr et al. |
| 7,303,548 B2 | 12/2007 | Rhad et al. |
| 7,322,963 B2 | 1/2008 | Goh |
| 7,387,616 B2 | 6/2008 | Li |
| 7,611,499 B2 | 11/2009 | Woehr et al. |
| 7,811,261 B2 | 10/2010 | Rubinstein et al. |
| 7,927,314 B2 | 4/2011 | Kuracina et al. |
| 7,935,080 B2 | 5/2011 | Howell et al. |
| 7,959,613 B2 | 6/2011 | Rhad et al. |
| 8,100,858 B2 | 1/2012 | Woehr et al. |
| 8,235,945 B2 | 8/2012 | Baid |
| 8,251,950 B2 | 8/2012 | Albert et al. |
| 8,545,454 B2 | 10/2013 | Kuracina et al. |
| 8,556,853 B2 | 10/2013 | Vaillancourt |
| 2001/0047156 A1 | 11/2001 | Parker |
| 2002/0111566 A1 | 8/2002 | Crawford et al. |
| 2003/0036731 A1 | 2/2003 | Wilkinson et al. |
| 2003/0105431 A1 | 6/2003 | Howell |
| 2003/0216687 A1 | 11/2003 | Hwang |
| 2003/0220587 A1 | 11/2003 | Swenson |
| 2003/0220612 A1 | 11/2003 | Hiejima |
| 2004/0049155 A1 | 3/2004 | Schramm |
| 2004/0049163 A1 | 3/2004 | Murashita |
| 2004/0167385 A1 | 8/2004 | Rioux et al. |
| 2004/0225262 A1 | 11/2004 | Fathallah et al. |
| 2005/0015054 A1 | 1/2005 | Chen |
| 2005/0119627 A1 | 6/2005 | Crawford |
| 2007/0100297 A1 | 5/2007 | Woehr et al. |
| 2008/0171986 A1 * | 7/2008 | Baid ........................ 604/164.08 |
| 2009/0131876 A1 | 5/2009 | Coyne |
| 2009/0163861 A1 | 6/2009 | Carlyon |
| 2010/0016804 A1 | 1/2010 | Muskatello et al. |
| 2010/0191188 A1 | 7/2010 | Harding et al. |
| 2010/0191189 A1 | 7/2010 | Harding et al. |
| 2010/0249707 A1 | 9/2010 | Woehr et al. |

FOREIGN PATENT DOCUMENTS

| | | |
|---|---|---|
| DE | 3802353 A1 | 8/1989 |
| EP | 0443735 A1 | 8/1991 |
| EP | 0747085 A2 | 12/1996 |
| EP | 0749761 A1 | 12/1996 |
| EP | 0750916 A2 | 1/1997 |
| EP | 0826388 A2 | 3/1998 |
| EP | 0995459 A2 | 4/2000 |
| EP | 1291035 A2 | 3/2003 |
| EP | 1369142 B1 | 8/2005 |
| EP | 1604700 A1 | 12/2005 |
| EP | 2016964 A1 | 1/2009 |
| EP | 2075029 A1 | 7/2009 |
| FR | 2767480 A1 | 2/1999 |
| JP | H04102462 A | 4/1992 |
| JP | 2002248168 A | 9/2002 |
| JP | 2002330946 A | 11/2002 |
| JP | 2002539897 T | 11/2002 |
| WO | 9211885 A1 | 7/1992 |
| WO | 9908742 | 2/1999 |
| WO | 0057940 A1 | 10/2000 |
| WO | 0069501 | 11/2000 |
| WO | 0156642 A1 | 8/2001 |
| WO | 03011381 A1 | 2/2003 |
| WO | 2004043521 A1 | 5/2004 |
| WO | 2006096633 A1 | 9/2006 |
| WO | 2006096634 A1 | 9/2006 |
| WO | 2006096635 A1 | 9/2006 |
| WO | 2006096636 A1 | 9/2006 |
| WO | WO 2006096634 A1 * | 9/2006 |
| WO | 2007022373 A2 | 2/2007 |

(56) References Cited

FOREIGN PATENT DOCUMENTS

| WO | 2010101573 A1 | 9/2010 |
|---|---|---|
| WO | 2010110789 A1 | 9/2010 |
| WO | 2012075402 A1 | 6/2012 |

OTHER PUBLICATIONS

Erskine, Canadian Application No. 2,599,943, Office Action dated Nov. 20, 2009, 2 pages.
Erskine, Chinese Application No. 200680007590, Office Action dated May 21, 2010, 4 pages.
Erskine, Australian Application No. 2006220691, Notice of Acceptance dated Jun. 9, 2010, 2 pages.
Erskine, Canadian Application No. 2,599,945, Office Action dated Nov. 13, 2009, 2 pages.
Erskine, Chinese Application No. 200680007484, Notification to Grant Patent Right dated Jun. 11, 2010, 4 pages.
Patent Cooperation Treaty, PCT/US06/07911, PCT International Search Report and Written Opinion, dated Jun. 23, 2006, 8 pages.
Patent Cooperation Treaty, PCT/US06/07911, PCT International Preliminary Report on Patentability, dated Feb. 12, 2007, 4 pages.
Erskine, U.S. Appl. No. 11/817,891, Office Communication dated Jun. 11, 2010, 11 pages.
Erskine, Australian Application No. 2006220692, Examiners First Report on Patent Application dated Oct. 21, 2008, 2 pages.
Erskine, Canadian Application No. 2,599,955, Office Action dated Mar. 5, 2010, 2 pages.
Erskine, Chinese Application No. 200680007485.0, Office Action dated Jun. 19, 2008, 6 pages.
Erskine, Chinese Application No. 200680007485.0, Notification to Grant Patent Right dated Jun. 4, 2010, 5 pages.
Erskine, Japanese Application No. P2008-500805, Office Action dated Apr. 20, 2010, 4 pages.
Erskine, Malaysia Application No. PI 20071465, Substantive Examination Report dated Apr. 30, 2010, 3 pages.
Patent Cooperation Treaty, PCT/US06/07912, PCT International Preliminary Report on Patentability, dated Sep. 20, 2007, 5 pages.
Patent Cooperation Treaty, PCT/US06/07912, PCT International Search Report and Written Opinion, dated Jun. 26, 2006, 8 pages.
Erskine, Taiwanese Application No. 095107584, Decision to Grant Patent dated Mar. 4, 2009, 5 pages.
Erskine, U.S. Appl. No. 11/817,687, Office Communication dated Jun. 30, 2010, 8 pages.
Erskine, U.S. Appl. No. 11/817,687, Office Communication dated Jan. 21, 2010, 9 pages.
Erskine, Australian Application No. 2006220689, Examiners First Report on Patent Application dated Jan. 15, 2009, 3 pages.
Erskine, Australian Application No. 2006220689, Patent Granted dated Jun. 18, 2010, 3 pages.
Erskine, Canadian Application No. 2,599,938, Office Action dated Feb. 23, 2010, 2 pages.
Erskine, Chinese Application No. 200680007548.2, Office Action dated Sep. 4, 2009, 4 pages.
Erskine, Chinese Application No. 200680007548.2, Notification to Grant Patent Right dated Jun. 12, 2010, 4 pages.
Erskine, Australian Application No. 2006220690, Notice of Acceptance dated Jun. 15, 2010, 3 pages.
Erskine, Japanese Application No. P2008-500802, Office Action dated Jun. 29, 2010, 6 pages.
Erskine, Malaysia Application No. PI 20071468, Substantive Examination Report dated Apr. 16, 2010, 2 pages.
Patent Cooperation Treaty, PCT/US06/07910, PCT International Preliminary Report on Patentability, dated Jul. 3, 2007, 20 pages.
Patent Cooperation Treaty, PCT/US06/07909, PCT International Search Report and Written Opinion, dated Jun. 26, 2006, 8 pages.
Erskine, Taiwanese Application No. 095107593, Decision to Grant Patent dated Dec. 11, 2009, 5 pages.
Patent Cooperation Treaty, PCT/US09/036197, PCT International Search Report and Written Opinion dated Apr. 28, 2009, 14 pages.

Patent Cooperation Treaty, PCT/US09/038246, PCT International Search Report and Written Opinion dated May 20, 2009, 11 pages.
Erskine, U.S. Appl. No. 11/817,891, Office Communication dated Oct. 19, 2009, 10 pages.
Erskine, Australian Application No. 2006220690, Examiner's First Report on Patent dated Nov. 11, 2008, 3 pages.
Erskine, Chinese Application No. 200680007590, Office Action (Translation) dated Aug. 21, 2009, 11 pages.
Erskine, European Application No. EP06737126, Supplementary European Search Report dated Feb. 11, 2010, 4 pages.
Patent Cooperation Treaty, PCT/US06/07910, PCT International Search Report and Written Opinion, dated Jul. 5, 2006, 8 pages.
OMGBA, Office Action Communication for U.S. Appl. No. 13/114,589 dated Sep. 14, 2012, 39 pages.
Shamsudin, Substantive/Modified Substantive Examination and Search Report, Application No. PI 20071467, Mar. 15, 2013, 4 pages.
Ehrsam, Supplementary European Search Report, Application No. EP 09 84 1250, Feb. 26, 2013, 5 pages.
OMGBA, Office Action Correspondence, U.S. Appl. No. 13/114,589, Apr. 10, 2013, 15 pages.
Desanto, Office Action Communication for U.S. Appl. No. 11/817,890 dated Jun. 6, 2013, 19 pages.
Patent Cooperation Treaty, International Preliminary Report on Patentability for PCT/US2011/063081 dated Jun. 4, 2013, 7 pages.
Patent Cooperation Treaty, International Preliminary Report on Patentability for PCT/US2011/063118 dated Jun. 4, 2013, 8 pages.
European Patent Office, Intention to Grant for EP Application No. 06 737 126.0 dated Jun. 17, 2013, 92 pages.
Canadian Patent Office, Notice of Allowance for CA Application No. 2,599,943 dated Jul. 3, 2013, 1 page.
Price, U.S. Appl. No. 11/817,891, Non-Final Office Action, Sep. 16, 2014, 94 pgs.
Desanto, Notice of Allowance and Fee(s) Due for U.S. Appl. No. 11/817,890 dated Sep. 17, 2013, 17 pages.
Matney, Office Action Communication for U.S. Appl. No. 13/254,163 dated Oct. 15, 2013, 81 pages.
OMGBA, Office Action Communication for U.S. Appl. No. 13/114,589 dated Oct. 31, 2013, 19 pages.
Patent Cooperation Treaty, Preliminary Report on Patentability and Written Opinion of the International Searching Authority for PCT/US2012/032578 dated Oct. 8, 2013, 10 pages.
Patent Cooperation Treaty, Notification of Transmittal of the International Search Report and the Written Opinion of the International Searching Authority, or the Declaration for PCT/US2011/063118 dated Apr. 3, 2012, 17 pages.
Patent Cooperation Treaty, Notification of Transmittal of the International Search Report and the Written Opinion of the International Searching Authority, or the Declaration for PCT/US2011/063081 dated Mar. 22, 2012, 10 pages.
Desanto, Office Action Communication for U.S. Appl. No. 11/817,890 dated Apr. 30, 2012, 14 pages.
Patent Cooperation Treaty, Notification of Transmittal of the International Search Report and the Written Opinion of the International Searching Authority, or the Declaration for PCT/US12/32578 dated Aug. 3, 2012, 26 pages.
European Patent Office, European Search Report for EP12169737 dated Jul. 25, 2012, 4 pages.
European Patent Office, European Search Report for EP12169713 dated Jul. 26, 2012, 5 pages.
European Patent Office, Supplementary European Search Report for EP09842422 dated Aug. 27, 2012, 7 pages.
Desanto, Office Action Communication for U.S. Appl. No. 11/817,890 dated Oct. 11, 2012, 26 pages.
Becamel, International Application No. PCT/US2009/036197, PCT International Preliminary Report on Patentability and Written Opinion of the International Searching Authority, Sep. 15, 2011, 10 pages.
Price, Office Action Communication for U.S. Appl. No. 11/817,892 dated Oct. 6, 2011, 14 pages.
Patent Cooperation Treaty, International Preliminary Report on Patentability and Written Opinion of the International Searching Authority for PCT/US2009/038246 dated Oct. 6, 2011, 7 pages.
Canadian Intellectual Property Office, Office Action for Application No. 2,599,943 dated Oct. 13, 2011, 2 pages.

(56) References Cited

OTHER PUBLICATIONS

IP Australia, Examiners First Report on Patent Application No. 2010203121 dated Nov. 4, 2011, 2 pages.
Erskine, Office Communication for U.S. Appl. No. 11/817,687 dated Dec. 9, 2010, 19 pages.
Erskine, Mexican Application No. MX/a/2007/010944, Office Action dated Mar. 11, 2011, 4 pages.
Erskine, Japanese Application No. JP07-5616-XY, Decision to Grant a Patent, dated Apr. 5, 2011, 6 pages.
Erskine, Taiwan Application No. 095107585, Office Action, dated Mar. 17, 2011, 3 pages.
Erskine, Mexian Application No. MX/a/2007/010946, Office Action, dated Apr. 2011, 2 pages.
Erskine, Japan Application No. P2008-500802, Notice of Reasons for Rejection, dated Apr. 5, 2011, 4 pages.
Erskine, China Application No. 201010109122.6, Office Action, dated Apr. 1, 2011, 11 pages.
Erskine, Office Action Communication for U.S. Appl. No. 11/817,892 dated Apr. 28, 2011, 25 pages.
Patent Cooperation Treaty, PCT Notification of Transmittal of International Preliminary Report on Patentability for PCT Application No. PCT/US06/07909 dated Aug. 16, 2007, 13 pages.
Erskine, Malaysia Application No. PI20071466, Office Action, dated Aug. 30, 2010, 3 pages.
Erskine, Taiwanese Application No. 095107587, Office Action dated Oct. 12, 2009, 12 pages.
Erskine, Australian Application No. 2006220691, Examiner's First Report on Patent dated Jan. 19, 2009, 2 pages.
Erskine, Chinese Application No. 200680007484, Office Action dated Aug. 21, 2009, 13 pages.
Erskine, Taiwanese Application No. 095107585, Office Action dated Apr. 6, 2009, 9 pages.
Erskine, Taiwanese Application No. 095107585, Office Action dated Oct. 15, 2009, 7 pages.
European Patent Office, European Search Report for Application No. EP06737125, dated Feb. 10, 2010, 7 pages.
Erskine, Canadian Application No. 2,599,943, Office Action dated Dec. 30, 2010, 2 pages.
Erskine, Canadian Application No. 2,599,945, Notice of Allowance dated Nov. 25, 2010, 1 pages.
Erskine, Canadian Application No. 2,599,955, Office Action dated Dec. 21, 2010, 3 pages.
Erskine, Canadian Application No. 2,599,938, Office Action dated Dec. 20, 2010, 2 pages.
Erskine, Japanese Application No. P2008-500805, Final Office Action dated Jan. 25, 2011, 25 pages.
Erskine, Japanese Application No. P2008-500804, Notice to Grant dated Feb. 2, 2011, 6 pages.
Desanto, Office Action Communication for U.S. Appl. No. 11/817,890 dated Aug. 31, 2011, 33 pages.
Osinski, Notice of Allowance & Fee(s) Due for U.S. Appl. No. 11/817,687 dated Jun. 30, 2011, 8 pages.
Erskine, Mexican Application No. MX/a/2007/010943, Office Action dated Jun. 10, 2011, 2 pages.
State Intellectual Property Office of the the People's Republic of China, Notification of the First Office Action for Application No. CN 201180066317 dated Oct. 27, 2014, 19 pages.
Price, Notice of Allowance and Fee(s) Due for U.S. Appl. No. 11/817,892 dated Dec. 19, 2014, 71 pages.
Flick: U.S. Appl. No. 13/259,715, filed Dec. 2, 2011, Office Action Dec. 17, 2012, 42pgs.
Final Office Action for U.S. Appl. No. 11/817,891, dated Jun. 9, 2015, 14 pages.
Office Action for JP Application No. 2014-504040, dated Jun. 30, 2015, 6 pages.
Office Action for CN Application No. 201180066317, dated Jun. 17, 2015, 5 pages.
Office Action for U.S. Appl. No. 13/997,969, dated Jul. 16, 2015, 85 pages.
Notice of Allowance and Fee(s) Due for U.S. Appl. No. 11/817,891, dated Aug. 25, 2015, 14 pages.
Communication Pursuant to Article 94(3) EPC for EP Application No. 12169713.0, dated Aug. 4, 2015, 5 pages.
Second Office Action for CN Application No. 201180066325.4, dated Jun. 16, 2015, 7 pages.

* cited by examiner

RELEASE MECHANISM FOR USE WITH NEEDLE SHIELDING DEVICES

CROSS REFERENCE TO RELATED APPLICATION

This patent application claims the benefit of U.S. Provisional Patent Application Ser. No. 61/419,005, filed Dec. 2, 2010.

BACKGROUND OF THE INVENTION

The invention relates generally to needle-based medical devices. More particularly, the invention relates to a passive safety shield for a needle of a needle-based medical device which shields the needle prior to releasing from a device. Needle shielding devices come in a variety of forms that do not allow for easy and passive activation and disconnection from a hub, such as a catheter introducer hub. Furthermore, needle shielding devices protrude into the catheter introducer hub and occupy the volume of the female luer connector, thereby interfering with hemostatic valves and seals.

BRIEF DESCRIPTION OF THE INVENTION

A first aspect of the disclosure provides a needle device comprising a hub having a longitudinal axis; a needle having a sharp distal tip; a needle shield assembly associated with the needle and moveable from a non-shielding position to a shielding position in which the sharp distal tip is covered by at least part of the needle shield assembly; a latch engaging with the hub when the needle shield assembly is in the non-shielding position; and a locking member operably connected to the needle shield assembly, and located at least partially within the hub when the needle shield assembly is in the non-shielding position, thereby locking the latch to the hub, and such that when the needle shield assembly moves into the shielding position, the locking member moves generally proximally, thereby unlocking the latch.

A second aspect of the disclosure provides a needle device comprising: a hub comprising a luer connector with a luer thread and having a longitudinal axis; a needle having a sharp distal tip; a needle shield assembly associated with the needle and moveable from a non-shielding position to a shielding position in which the sharp distal tip is covered by at least part of the needle shield assembly, a latch engaging with the luer thread of the hub when the needle shield assembly is in the non-shielding position, a locking member operably connected to the needle shield assembly and located at least partially in the luer connector when the needle shield assembly is in the non-shielding position, thereby locking the latch to the hub, and such that when the needle shield assembly moves into the shielding position, the locking member moves axially.

A third aspect of the disclosure provides a method of manufacturng a needle assembly comprising: placing a blocking object in a carrier, wherein the carrier includes a flange disposed on a distal end thereof; inserting the carrier into a shroud; inserting the shroud into a housing until the proximal end of the shroud abuts a reduced diameter portion at a proximal end of the housing, wherein the housing includes a hooked member circumferentially extending from a portion of a distal end of the housing, and a first, distal opening and a second, proximal opening are provided through a wall of the housing; inserting a proximal end of a needle into an axial lumen of the carrier, thereby displacing the blocking object such that it protrudes at least partially through the proximal, second opening in the housing; affixing the proximal end of the needle to a needle hub; threading a catheter hub and a cannula over a distal end of the needle, wherein the catheter hub has a flanged proximal end; and engaging the hooked member with the flanged proximal end of the catheter hub, and inserting the flange disposed on the distal end of the carrier into the catheter hub, wherein the engaging and inserting the flange causes the blocking object to move distally such that it protrudes from the first, distal opening in the housing.

These and other aspects, advantages and salient features of the invention will become apparent from the following detailed description, which, when taken in conjunction with the annexed drawings, where like parts are designated by like reference characters throughout the drawings, disclose embodiments of the invention.

Figure 1:
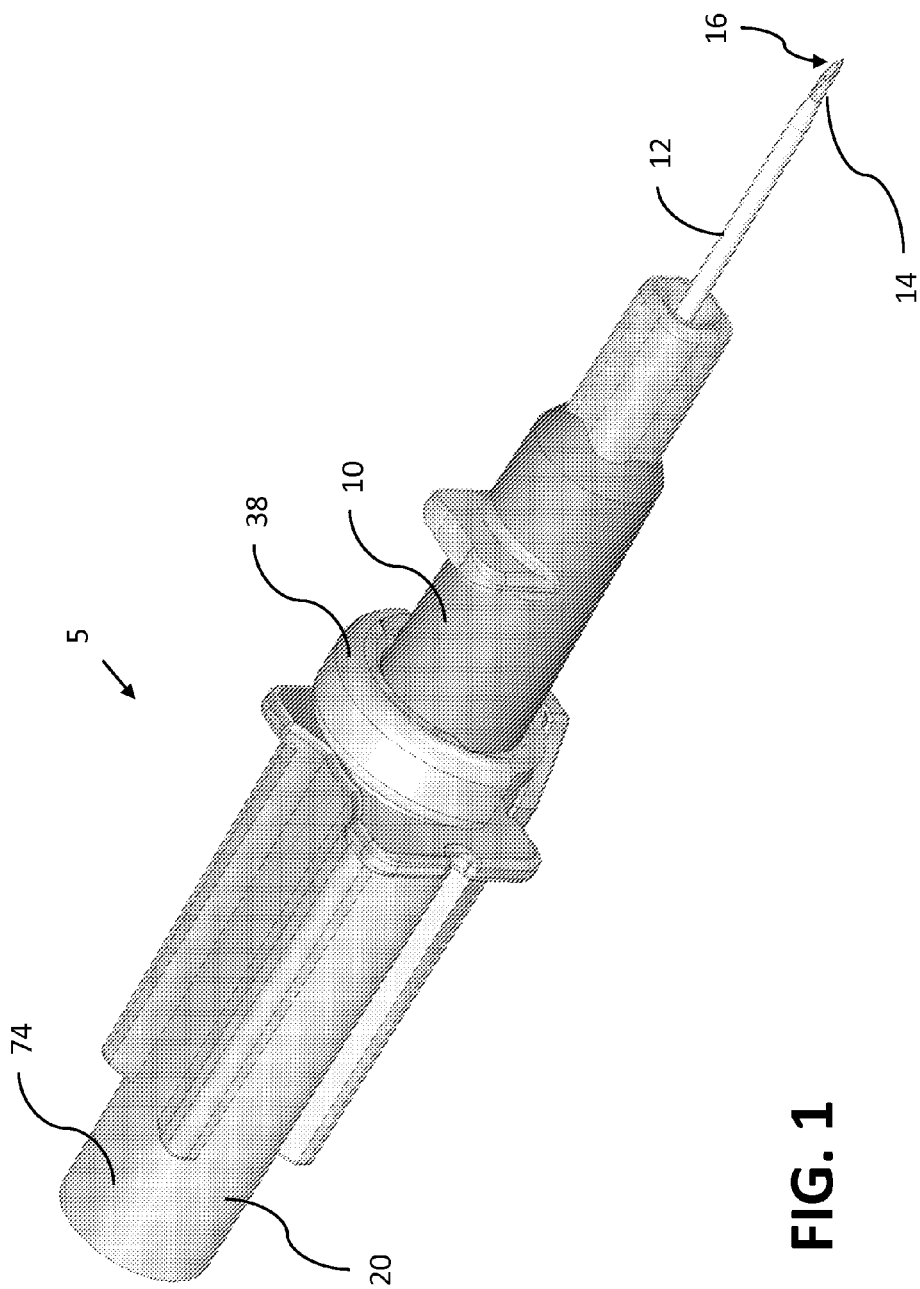
FIG. 1 shows a perspective view of a needle device including a needle shield assembly in a non-shielding position according to embodiments of the invention.

It is noted that the drawings of the disclosure are not necessarily to scale. The drawings are intended to depict only typical aspects of the disclosure, and therefore should not be considered as limiting the scope of the disclosure. In the drawings, like numbering represents like elements between the drawings.

DETAILED DESCRIPTION OF THE INVENTION

As noted, a needle-based medical device including a needle shield 30 (FIG. 5) will be described with reference to FIGS. 1-15. At least one embodiment of the present invention is described below in reference to its application in connection with a needle-based medical device in the form of a catheter introducer. Although embodiments of the invention are illustrated relative to a needle-based medical device in the form of a catheter introducer, it is understood that the teachings are equally applicable to other needle-based medical devices including, but not limited to, syringes, blood collection devices, and other types of devices. Further, at least one embodiment of the present invention is described below in reference to a nominal size and including a set of nominal dimensions. However, it should be apparent to those skilled in the art that the present invention is likewise applicable to any suitable needle-based device. Further, it should be apparent to those skilled in the art that the present invention is likewise applicable to various scales of the nominal size and/or nominal dimensions.

Figure 2:
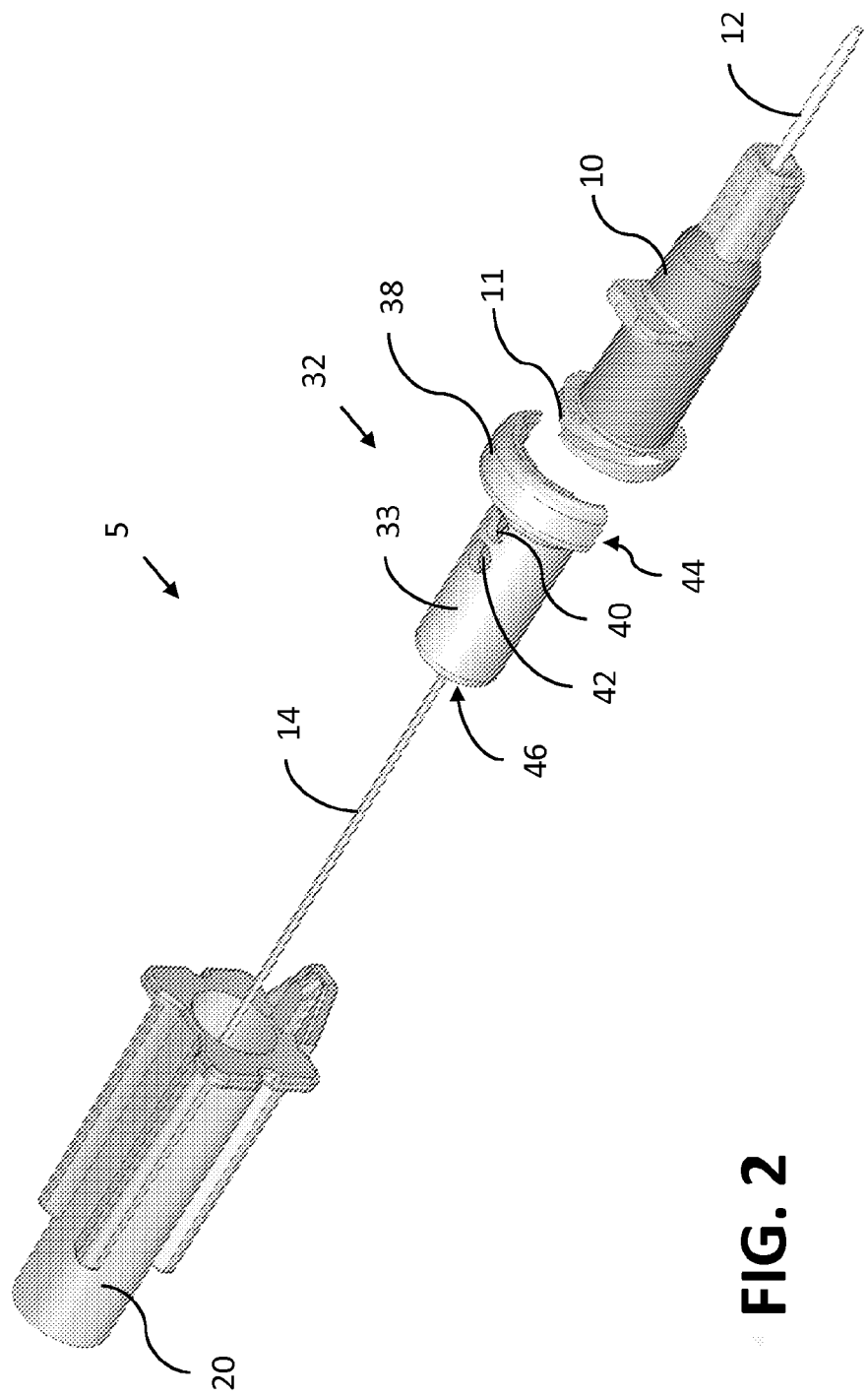
FIG. 2 shows an exploded perspective view of a needle device including a needle shield assembly according to embodiments of the invention.
Figure 3:
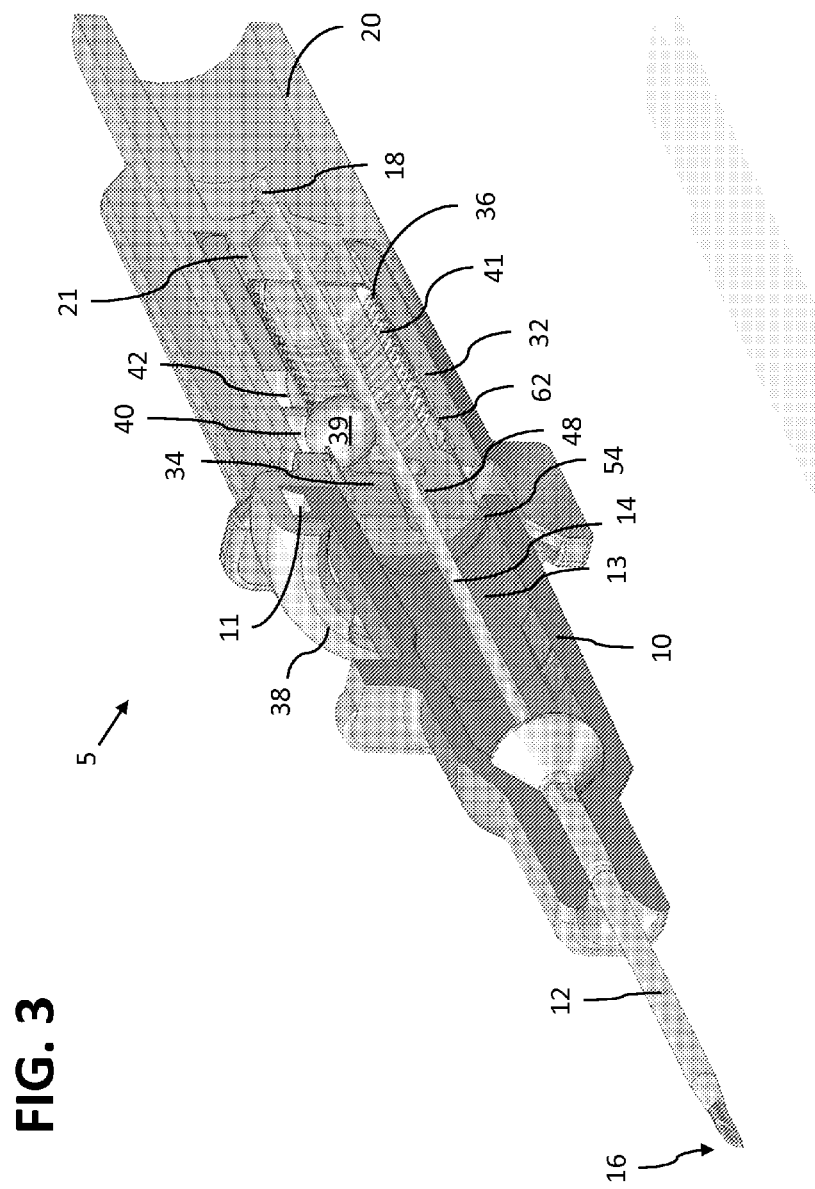
FIG. 3 shows a cutaway perspective view of a needle device including a needle shield assembly in a non-shielding position according to embodiments of the invention.

With reference to FIGS. 1-3, one embodiment is illustrated including a needle device 5 in the form of a catheter introducer assembly including a hub 10, a catheter cannula 12, and an introducer needle 14.

In the embodiment shown in FIG. 2, hub 10 includes a threaded proximal end 11 to which tubing and the like can be connected. Hub 10 also may include a female luer adapter 13 (FIGS. 3-4) into which a male component such as a blood sealing device 15 (FIGS. 5-10) such as a valve or septum can be placed within hub 10. Although not shown, hub 10 may also include a port. Needle 14 includes a longitudinal axis 17 (FIG. 5), a sharp distal end 16, and a proximal end 18 (FIG. 3).

Figure 4:
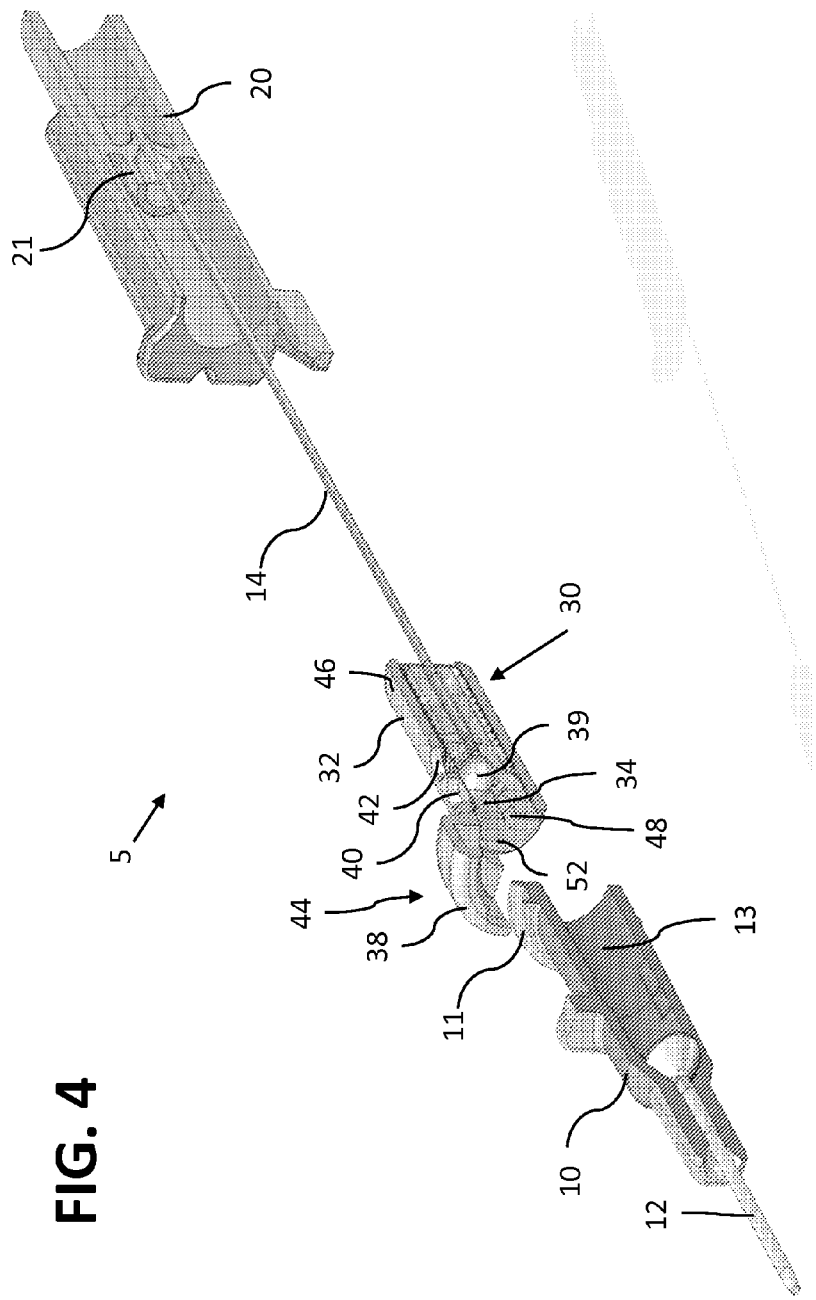
FIG. 4 shows an exploded cutaway perspective view of a needle device including a needle shield assembly in a non-shielding position according to embodiments of the invention.
Figure 5:
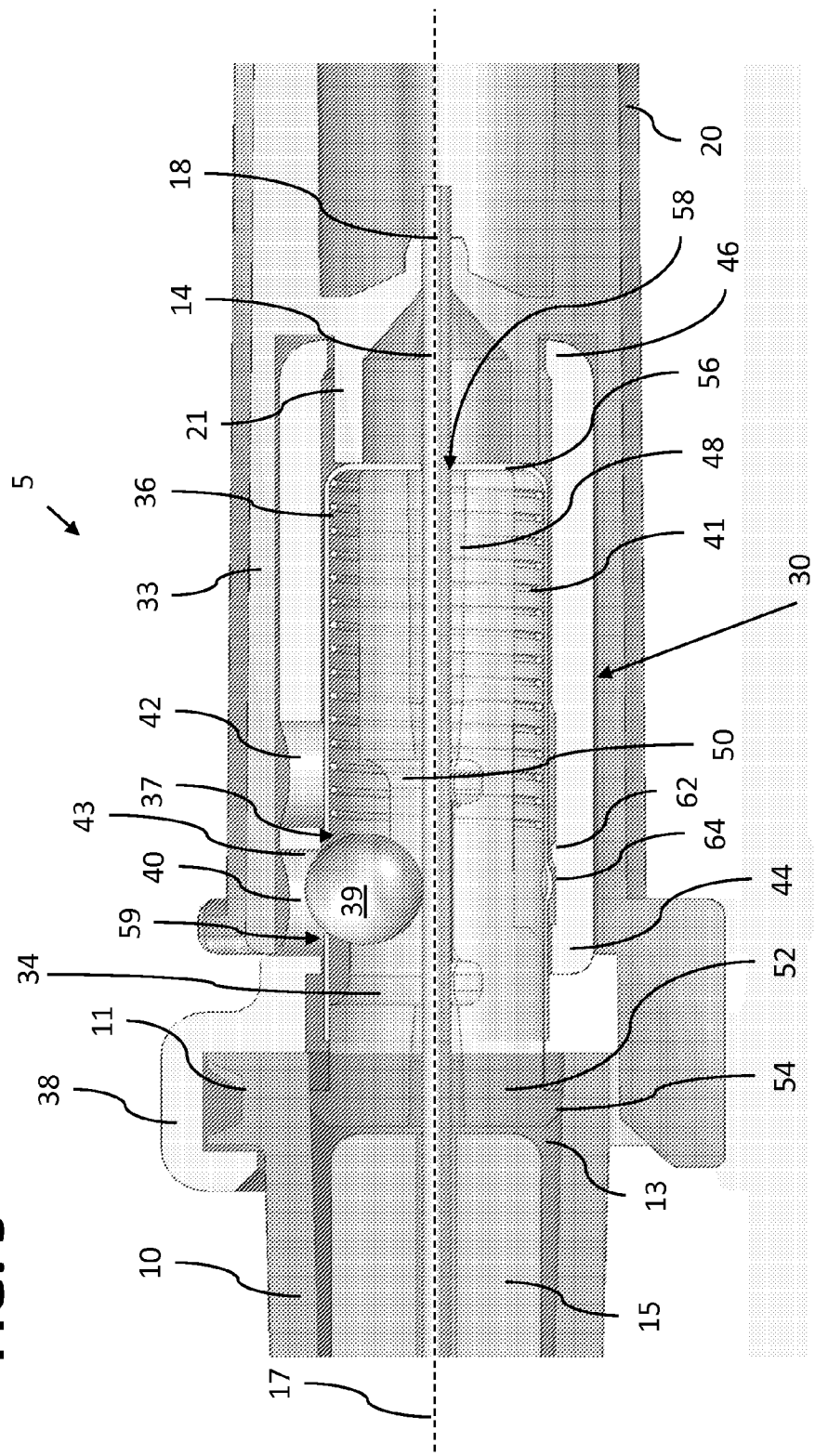
FIG. 5 shows a detailed cross-sectional view of the needle shield assembly and hub in a non-shielding position according to embodiments of the invention.
Figure 6:
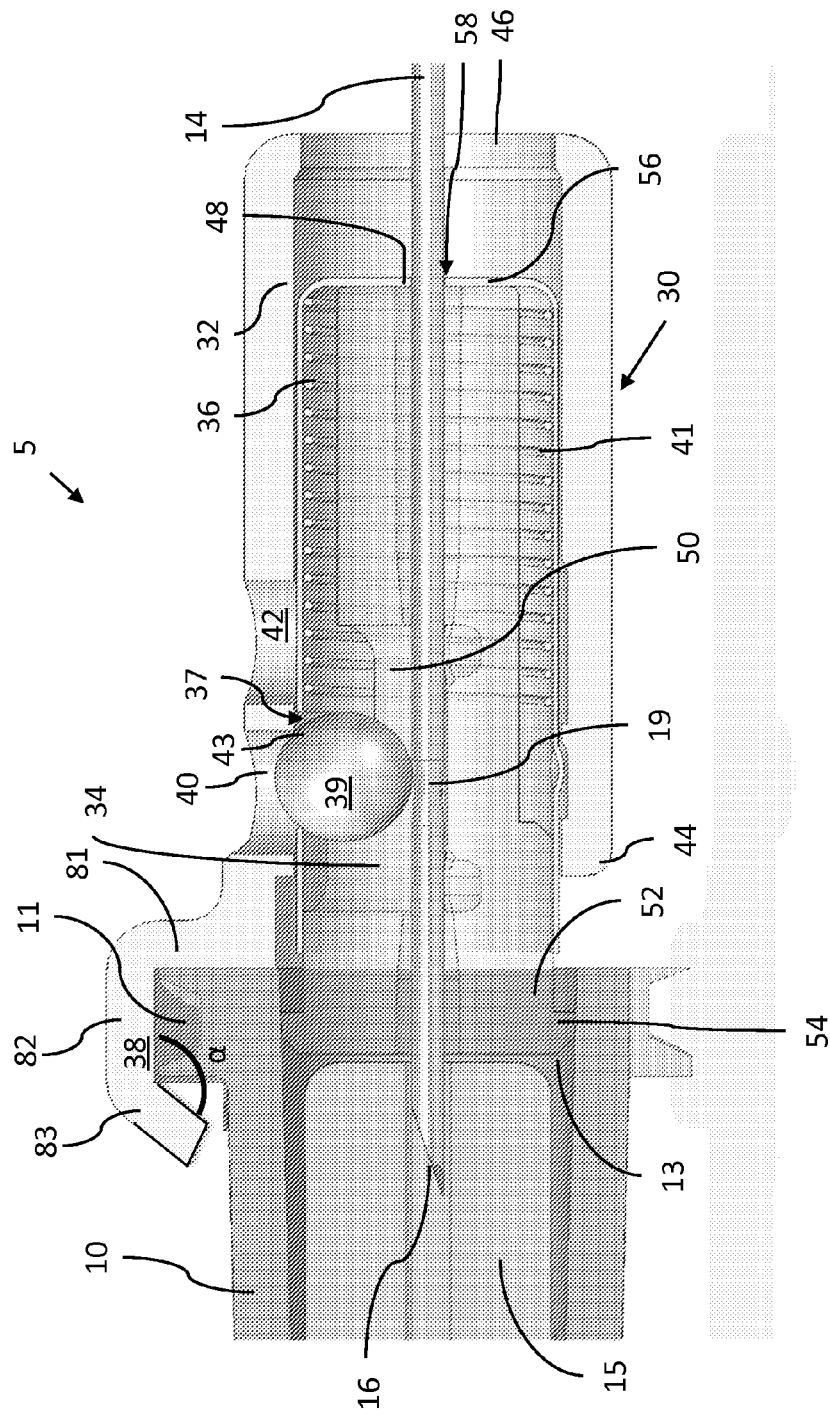
FIG. 6 shows a detailed cross-sectional view of the needle shield assembly in an intermediate non-shielding position according to embodiments of the invention.
Figure 7:
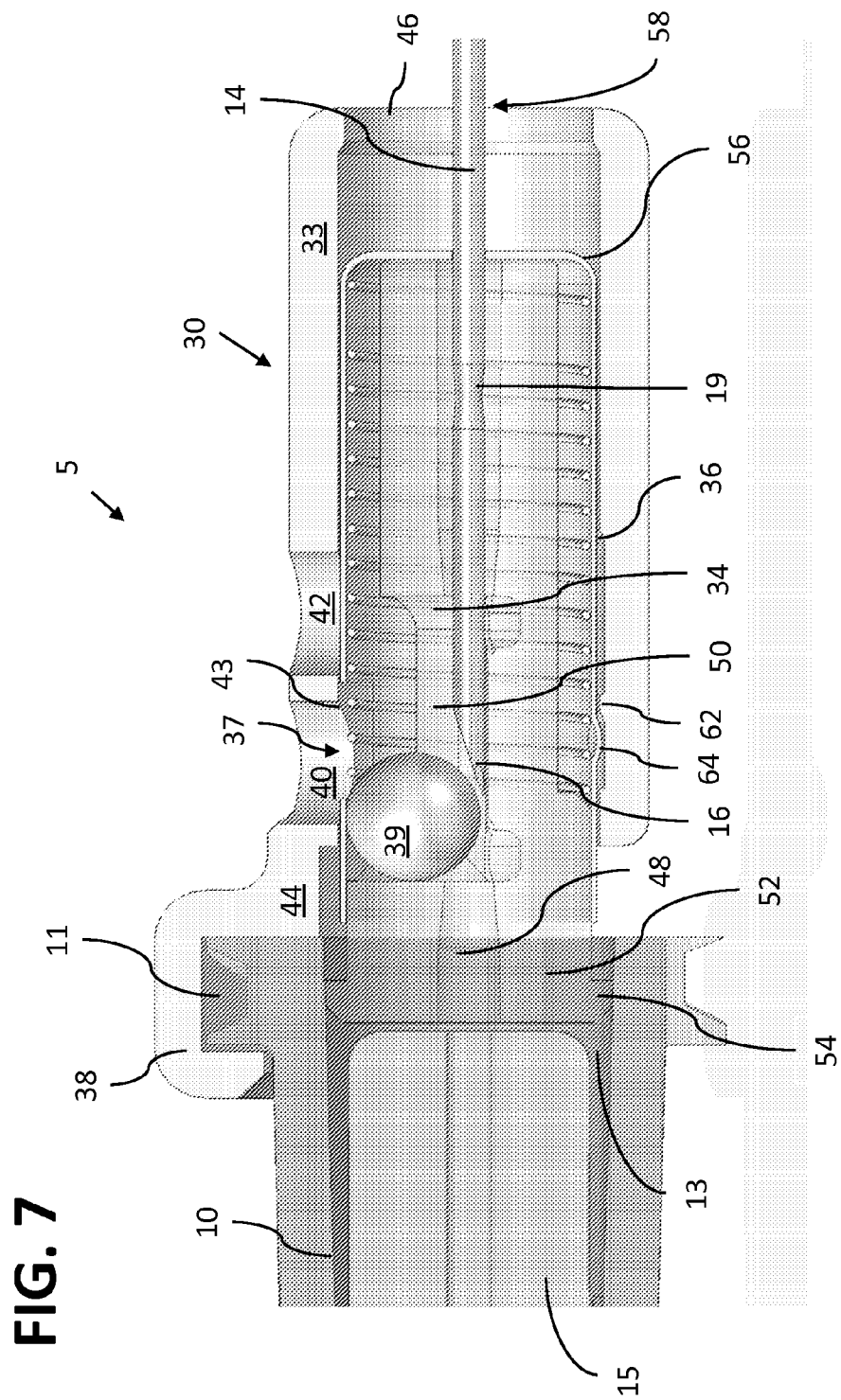
FIG. 7 shows a detailed cross-sectional view of the needle shield assembly in an intermediate shielding position according to embodiments of the invention.

As shown in FIGS. 3-5, proximal end 18 of needle 14 is secured to a distal end of needle hub 20, e.g., by glue using a glue well, which is described in co-pending US patent applications publications No. 2009/0036843A1 and No. 2009/0032185A1, each of which are incorporated herein by reference. Needle hub 20 may be secured at its proximal end to a handle 74. Needle 14, hub 10, cannula 12, and needle hub 20 may be substantially coaxial.

Referring to FIGS. 3-10, needle shield assembly 30 and a latch 32 are provided for shielding distal tip 16 of needle 14. Needle shield assembly 30 includes a needle blocking object 39, and a carrier 34 for carrying needle blocking object 39. Needle shield assembly 30 may further include an external shroud 36 disposed about carrier 34 and within latch 32, and a spring 41 for biasing needle blocking object 39 as described herein.

Needle shield assembly 30 is movable between a non-shielding position (FIGS. 3, 5-6) and a shielding position (FIGS. 7-10). FIGS. 5-10 illustrate one embodiment of progression from the non-shielding position, in which latch 32 and locking member 54 retain the needle shield assembly 30 in engagement with hub 10, to the shielding position, in which needle shield assembly 30 prevents emergence of sharp distal end 16 of needle 14 therefrom.

With reference to FIG. 5, needle shield assembly 30 will now be described. Needle shield assembly 30 includes carrier 34, which may be substantially cylindrical and includes an axial lumen 48 substantially aligned with a longitudinal axis of the device. Axial lumen 48 accommodates needle 14 and allows carrier 34 to slide along needle 14. Carrier 34 may further include an internal member including a channel 50 or other structure for limiting radial movement of needle blocking object 39 toward the longitudinal axis of needle 14 in the shielding position of needle shield assembly 30. In the illustrative embodiment, channel 50 is shaped and dimensioned such that needle blocking object 39 can be carried and can moved along channel 50 (FIGS. 5-10) and dropped into place in the shielding position (FIGS. 7-10). In the shielding position, needle blocking object lies at least partially across axial lumen 48, thereby blocking emergence of sharp distal end 16 of needle 14. In still further embodiments, carrier 34 may include an external shroud 36. Shroud 36 may be made of metal, and may be substantially cup-shaped, such that it substantially encases carrier 34, but is open at the distal end 60. Carrier 34 can thus be inserted into shroud 36 such that a proximal end of the carrier abuts the inside of proximal end 56 of shroud 36. Carrier 34 also includes a first opening 37 through which a portion of needle blocking object projects 39 while resting in channel 50 in a non-shielding position. In embodiments including shroud 36, opening 37 extends through a thickness of a wall of shroud 36.

A spring 41 may further be provided for biasing needle blocking object 39. Spring 41 may be disposed about carrier 34, and within shroud 36, such that it abuts needle blocking object 39. Spring 41 tends to urge needle blocking object distally and into lumen 48, toward the axis of the device. Spring 41 may be, for example, a coil spring, although other types of springs may be used as known in the art.

A locking member 54 may be operably coupled to a distal end 52 of carrier 34, and is dimensioned to engage an internal surface of hub 10 in the non-shielding position. Locking member 54 may be a flange or flanged member. In some embodiments, the engagement between an internal surface of hub 10 and locking member 54 may include insertion of at least a portion of locking member 54 into hub 10 as shown in FIG. 5. As noted, hub 10 may include a female luer adapter 13, which engages with a close slip fit with locking member 54.

Figure 8:
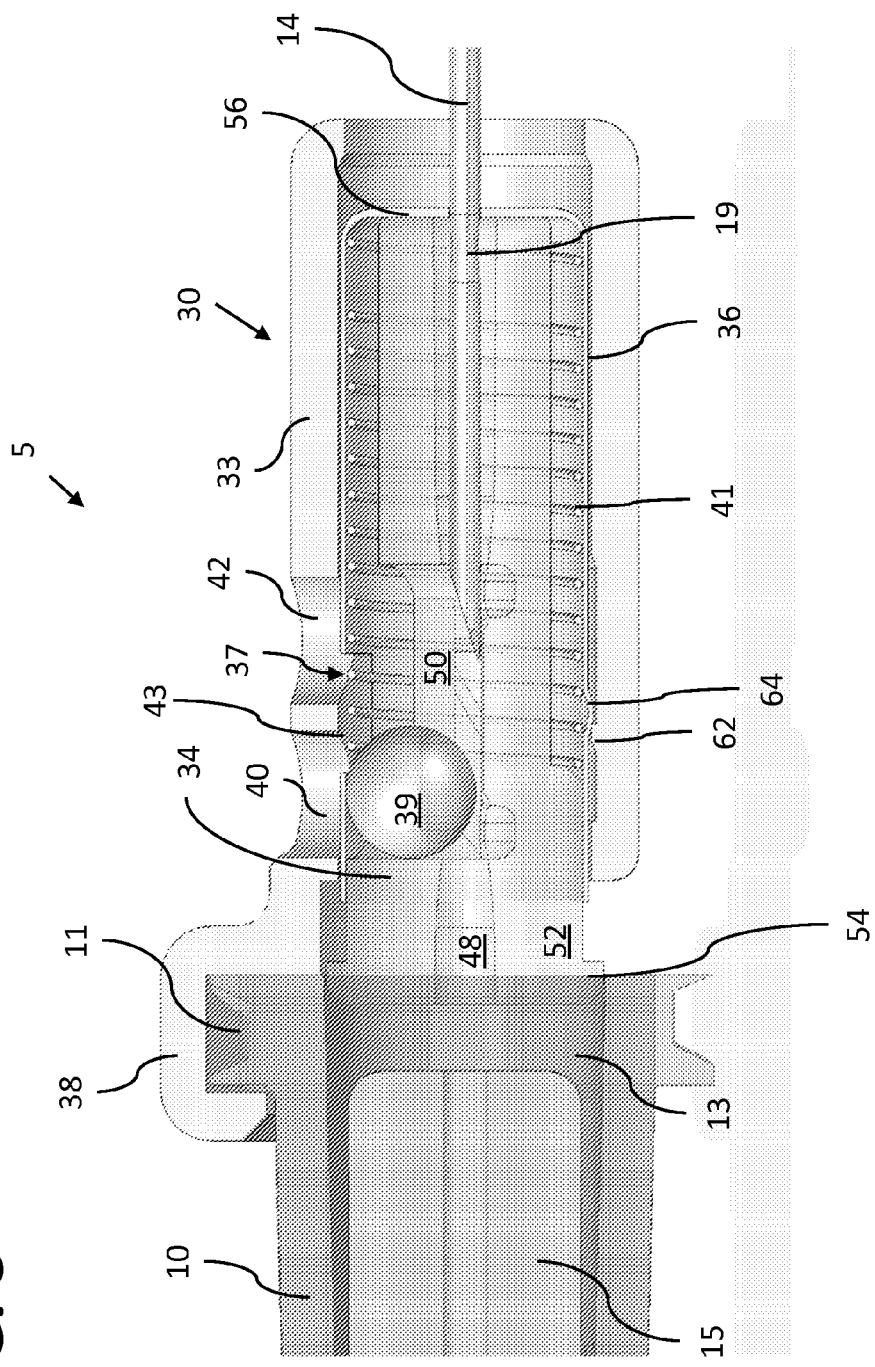
FIG. 8 shows a detailed cross-sectional view of the needle shield assembly in an intermediate shielding position according to embodiments of the invention.
Figure 9:
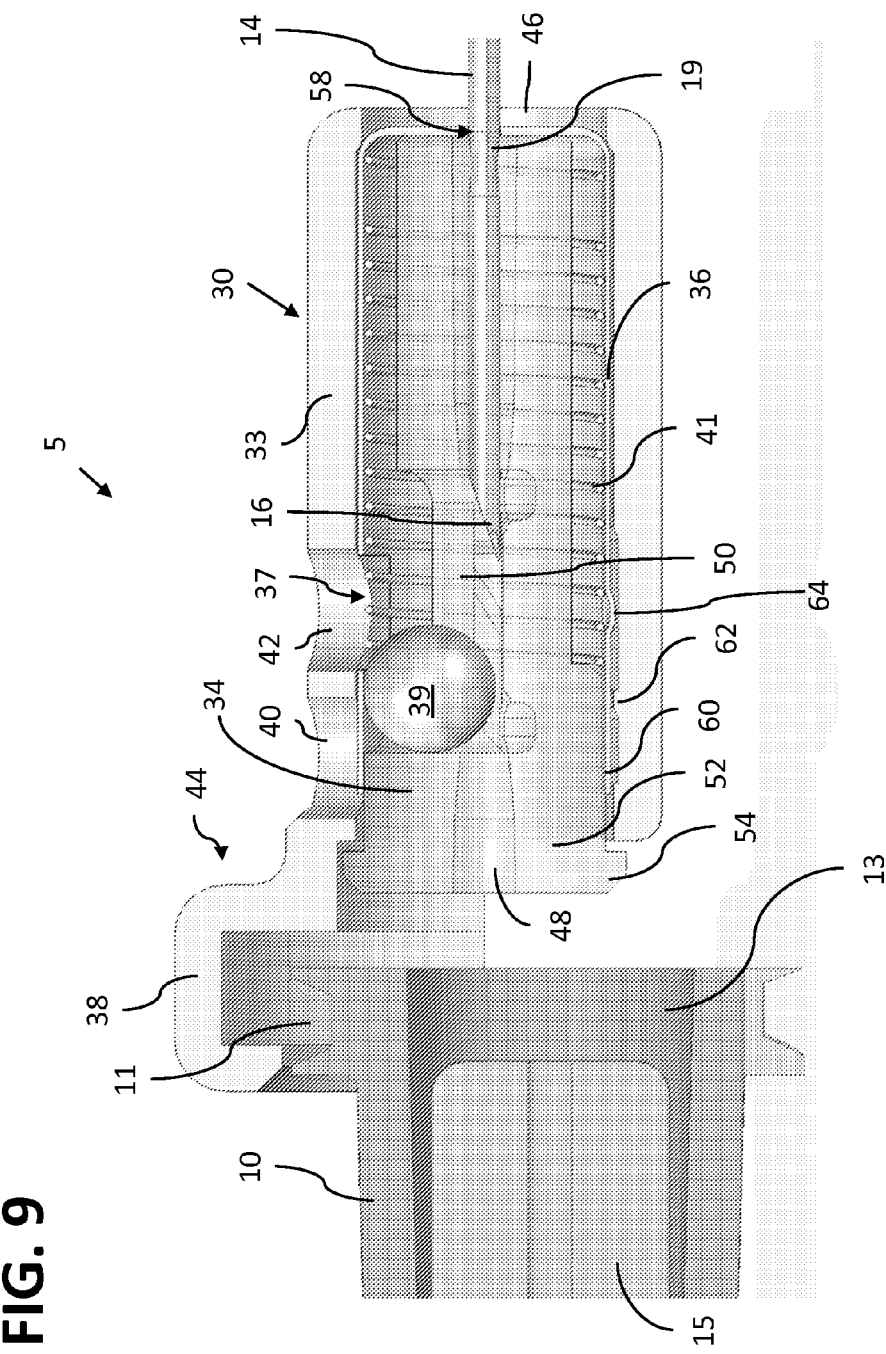
FIG. 9 shows a detailed cross-sectional view of the needle shield assembly in an intermediate shielding position according to embodiments of the invention.
Figure 10:
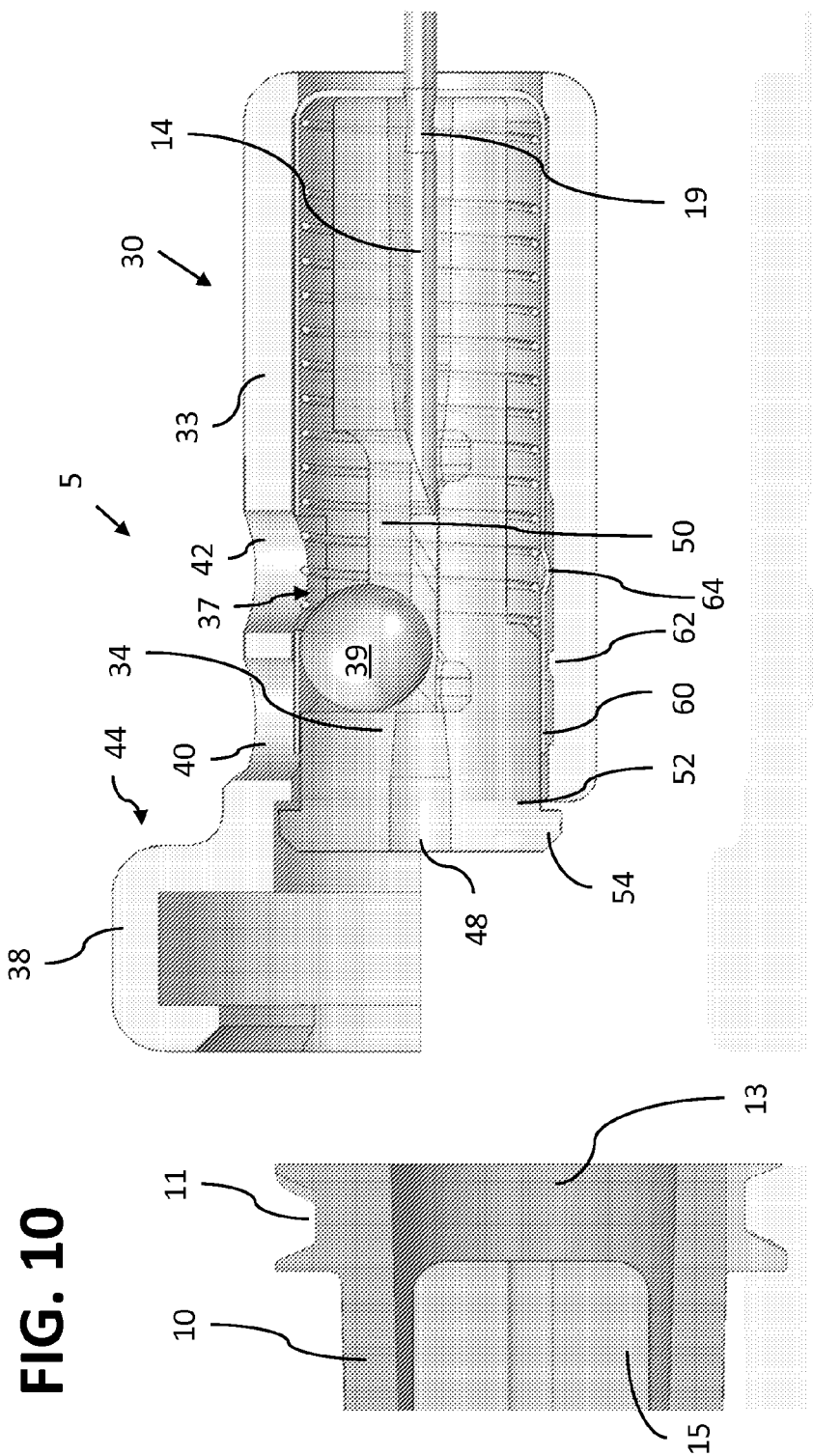
FIG. 10 shows a detailed cross-sectional view of the needle shield assembly in a shielding position according to embodiments of the invention.
Figure 11:
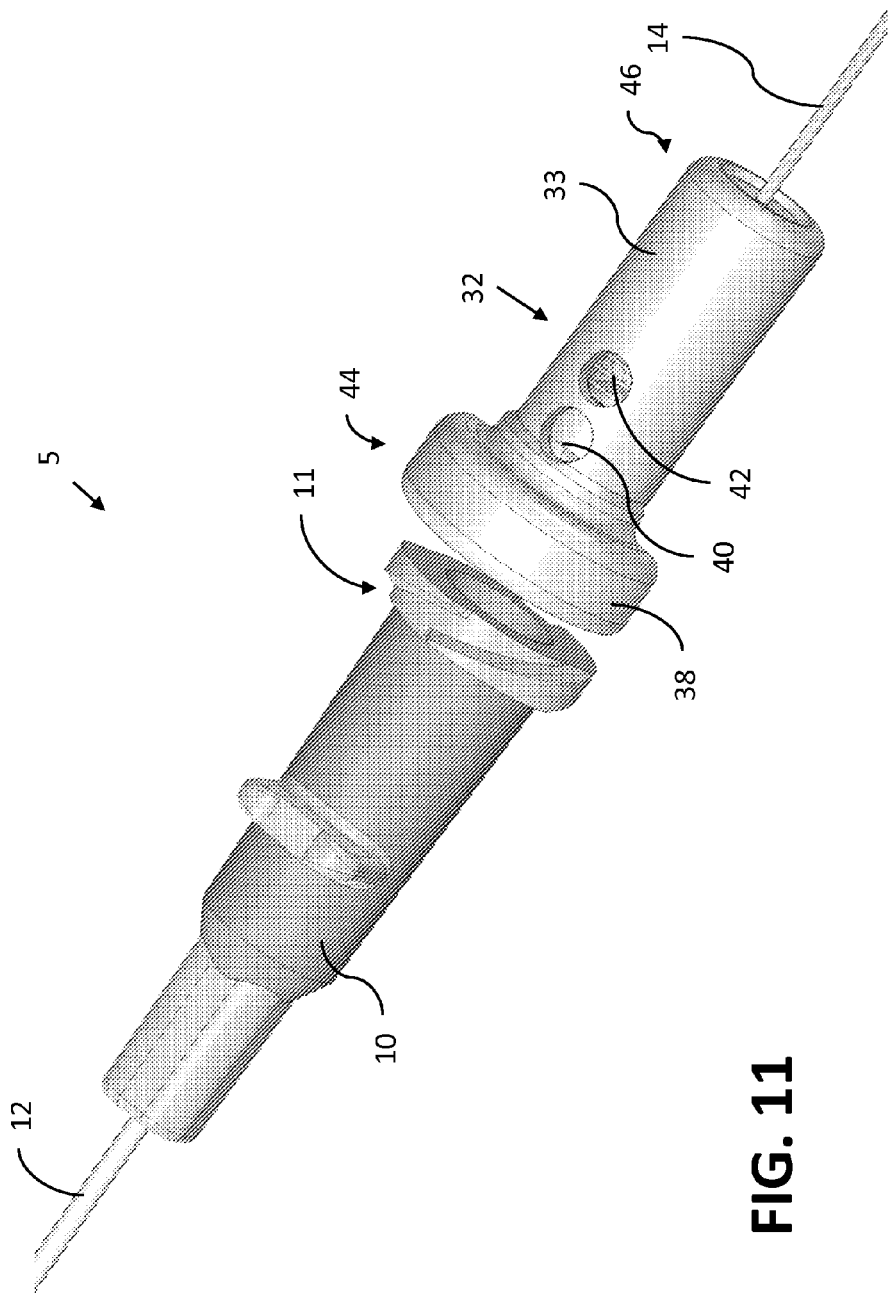
FIG. 11 shows an exploded perspective view of a needle device including a needle shield assembly according to embodiments of the invention.

In an embodiment, at a proximal end of axial lumen 48, a hole or opening 58 (FIGS. 5-6) may be provided in carrier 34 including shroud 36. Hole 58 is dimensioned to accommodate the outer diameter of needle 14. Needle 14 may include a crimp 19, shown in FIG. 6, which provides an area of needle 14 having enlarged diameter in at least one radial direction. Opening 58 does not accommodate crimp 19, so that as shown in FIG. 8, crimp 19 provides a stop which engages an inside of proximal end 56 of shroud 36. Crimp 19 is positioned along needle 14 such that when crimp 19 reaches proximal end 56 of shroud 36, sharp distal tip 16 of needle 14 is proximal of needle blocking object 39, and therefore shielded.

As further shown in FIG. 5, carrier 34 may be disposed substantially within latch 32, the latter of which engages hub 10 to needle shield assembly 30 in the non-shielding position. Latch 32 includes a housing 33 having a proximal end 46 and a distal end 44, the latter of which is coupled to a hooked latch member 38. Latch member 38 and housing 33 are shown in FIG. 5 as being a single, continuous member, but embodiments in which latch member 38 and housing 33 are separate members that are operably connected are also considered part of the invention.

Figure 12:
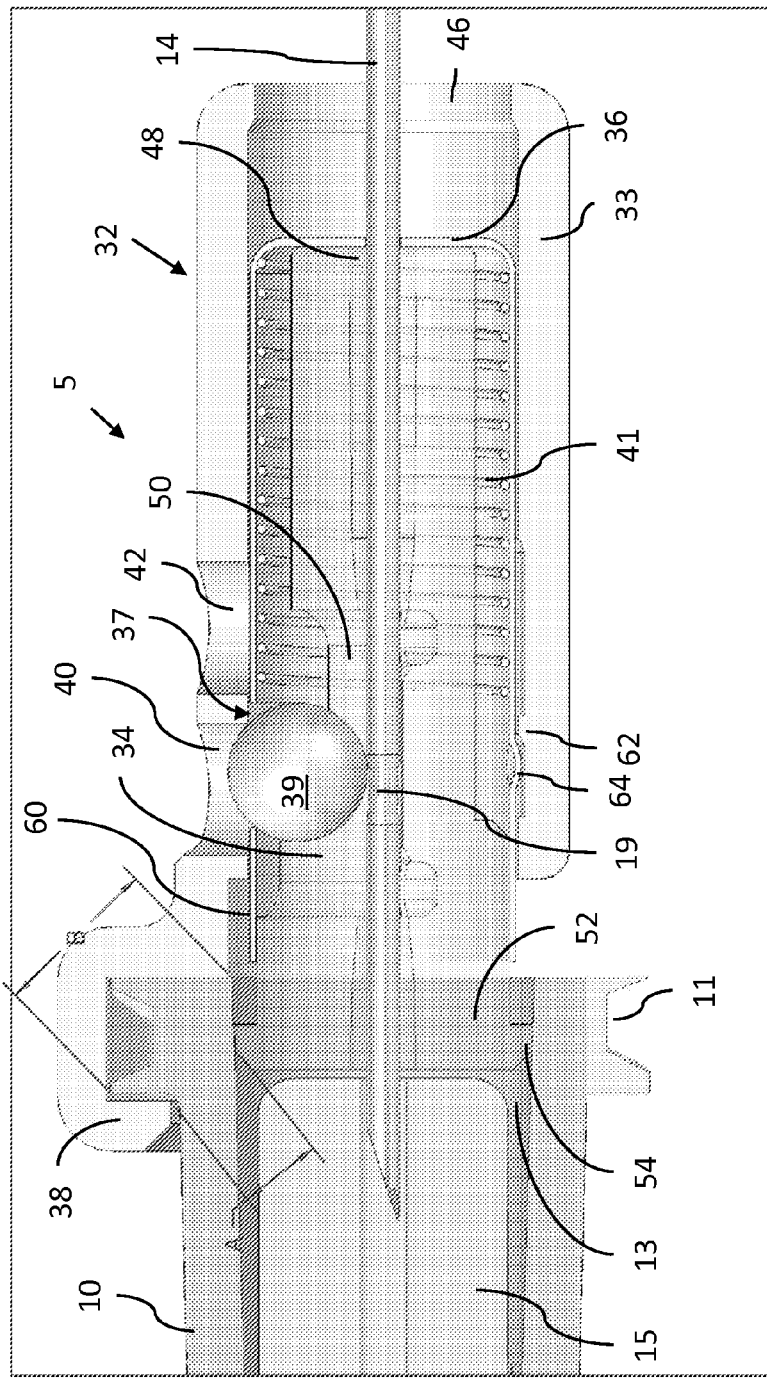
FIG. 12 shows a detailed cross-sectional view of the needle shield assembly in an intermediate non-shielding position according to embodiments of the invention.

Latch member 38 is shaped and dimensioned to engage with flanged proximal end 11 of hub 10. As shown in FIGS. 3 and 12, latch member 38 includes a hooked leg extending over a flange on flanged proximal end 11 of hub 10. In one embodiment, hooked latch member 38 includes a first member 81 extending radially outward relative to housing 33, a second member 82 extending distally from a radially outward end of first member 81 in a direction substantially parallel to housing 33, and a third member 83 extending radially inward from the distal end of second member 82, forming a distal restraining surface of latch 32. In one embodiment, shown in FIG. 5, second member 82 and third member 83 may be orthogonal. In an alternative embodiment, shown in FIG. 6, the angle α formed by second member 82 and third member 83 may be other than orthogonal, e.g., about 135°, such that third member 83 provides a beveled edge on the distal restraining surface of latch 32 for releaseably engaging flanged proximal end 11 of hub 10. With reference to FIG. 12, in one embodiment, a first distance A between a radially inward end of the leg of latch member 38 and distal end 52 of locking member 54 as positioned within hub 10 is less than a second distance B between a proximal-most point on an internal diameter of hub 10 and a distal-most point on an external diameter of the flange on proximal end 11 of hub 10. The above-described angled structure may be provided to enable smooth disengagement of hook member 38 and flanged proximal end 11.

In some embodiments, flanged proximal end 11 of hub 10 may be threaded. Latch member 38 may have an extent that varies between about 90° and 180° circumferentially such that latch 32 can engage hub 10 regardless of position relative to threads on flanged proximal end 11 of hub 10, and still be able to freely disengage from hub 10 in the shielding position.

Latch 32 further includes a first opening 40 extending through a wall thereof. In the non-shielding position, shown in FIGS. 5-6, opening 37 in external shroud 36 substantially aligns with first opening 40 in latch 32 in the non-shielding position, such that at least a portion of needle blocking object 39 protrudes through opening 37 and into first opening 40. The protruding portion of needle blocking object 39 engages a proximal edge 43 of first opening 40 in latch 32 to engage locking member 54 with the internal surface of hub 10 and maintain latch 32 in engagement with hub 10.

FIGS. 7-10 illustrate the continued progression of movement from the non-shielding position to the shielding position. Upon movement of the needle shield assembly 30 from the non-shielding position to the shielding position, needle blocking object 39 exits first opening 40 in latch 32 and opening 37 in carrier 34. Needle blocking object 39 does so under a force from spring 41, which biases needle blocking object 39 distally and toward longitudinal axis 17 of needle 14. Needle blocking object 39 at least partially enters axial lumen 48, preventing emergence of sharp distal end 16 of needle 14 from carrier 34. Locking member 54 disengages from hub 10 and moves proximally within latch 32, allowing latch 32 to disengage hub 10 from needle shield assembly 30.

Latch 32 may further include a second opening 42 through a wall of housing 33. Second opening 42 is disposed proximally of first opening 40.

In further embodiments, as shown in FIGS. 5-10, latch 32 may include a first protrusion 62 on an inner surface of housing 33. A second protrusion 64 may be disposed on an outer surface of carrier 34. Where carrier 34 includes external shroud 36 encasing carrier 34, second protrusion 64 may be on, or part of, an outer surface of external shroud 36. First protrusion 62 interacts with second protrusion 64 as needle shield assembly 30 moves proximally from a non-shielding position to a shielding position such that a pull-out force required to move carrier 34 proximally relative to latch 32 is greater than a frictional force between needle blocking object 39 and needle 14. This structure prevents wedging of blocking object 39 and needle 14, as blocking object 39 can roll under proximal edge 43 of opening 40 in latch 32 and wedge against needle 14.

As shown in FIGS. 1-5, needle hub 20 may be disposed about latch 32. Needle 14 is coupled to needle hub 20 such that when needle hub 20 is pulled in a proximal direction, needle 14 moves proximally toward a shielding position. Needle hub 20 may include a boss 21 that abuts proximal end 56 of shroud 36.

When the needle shield assembly is in its fully assembled, non-shielding state (FIGS. 5-6) locking member 54 fits closely into female luer 13 in hub 10. Latch 32, and particularly latch member 38, is hooked over proximal end 11 of hub 10. The fit between latch member 38 and proximal end 11 of hub 10 is loose, such that the pull-off force is low. Needle blocking object 39 partially protrudes through opening 37 and into first opening 40 in latch 32. Needle blocking object 39 abuts distal edge 59 of opening 37 and proximal edge 43 of opening 40, and is held in place by abutment with the outer surface of needle 14. Locking member 54 cannot escape hub 10 due to needle blocking object 39 abutting with proximal edge 43 of first opening 40.

When needle shield assembly 30 is deployed (i.e., needle 14 is withdrawn from hub 10 and carrier 34 moves into the shielding position shown in FIGS. 7-10), the user pulls needle hub 20 in a proximal direction, thus drawing needle 14 along cannula 12 and carrier 34, until crimp 19 abuts opening 58 in shroud 36. At that point, sharp distal tip 16 of needle 14 has passed needle blocking object 39, and needle blocking object 39 has moved into lumen 48, urged there by spring 41 (turning about distal edge 59 of opening 37 in shroud 36), thereby blocking the path of sharp distal tip 16 of needle 14, should needle 14 move in the distal direction. Locking member 54 can now move out of hub 10 and deeper, or proximally, into latch 32, since needle blocking object 39 is no longer obstructed by proximal edge 43 of first opening 40. This movement also releases latch member 38, so it can disengage with proximal end 11 of hub 10.

The combination of needle blocking object 39, needle 14, openings 37 in shroud 36 and first opening 40 in latch 32, and locking member 54 (on carrier 34) forms a locking assembly, which secures needle shield assembly 30 to hub 10. This locking assembly is only released when sharp distal tip 16 of needle 14 has passed needle blocking object 39 and is thus shielded, thereby providing a passive safety shield which cannot disengage from hub 10 prior to shielding sharp distal tip 16 of needle 14. Needle shield assembly 30 is substantially external of hub 10 in this position, thus providing space within hub 10 for a blood sealing device 15, for example a septum or a luer-actuated valve, as well as a side port.

The combination of crimp 19 and opening 37 in shroud 36 prevents proximal movement of sharp distal tip 16 of needle 14. This and other ways of preventing proximal movement of the needle 14 are shown in co-pending US patent applications No. 2008/0119795 A1, No. 2009/0137958 A1 and 2009/0249605 A1, each of which are incorporated herein by reference.

A method of assembling or manufacturing the device will now be described.

Figure 13:
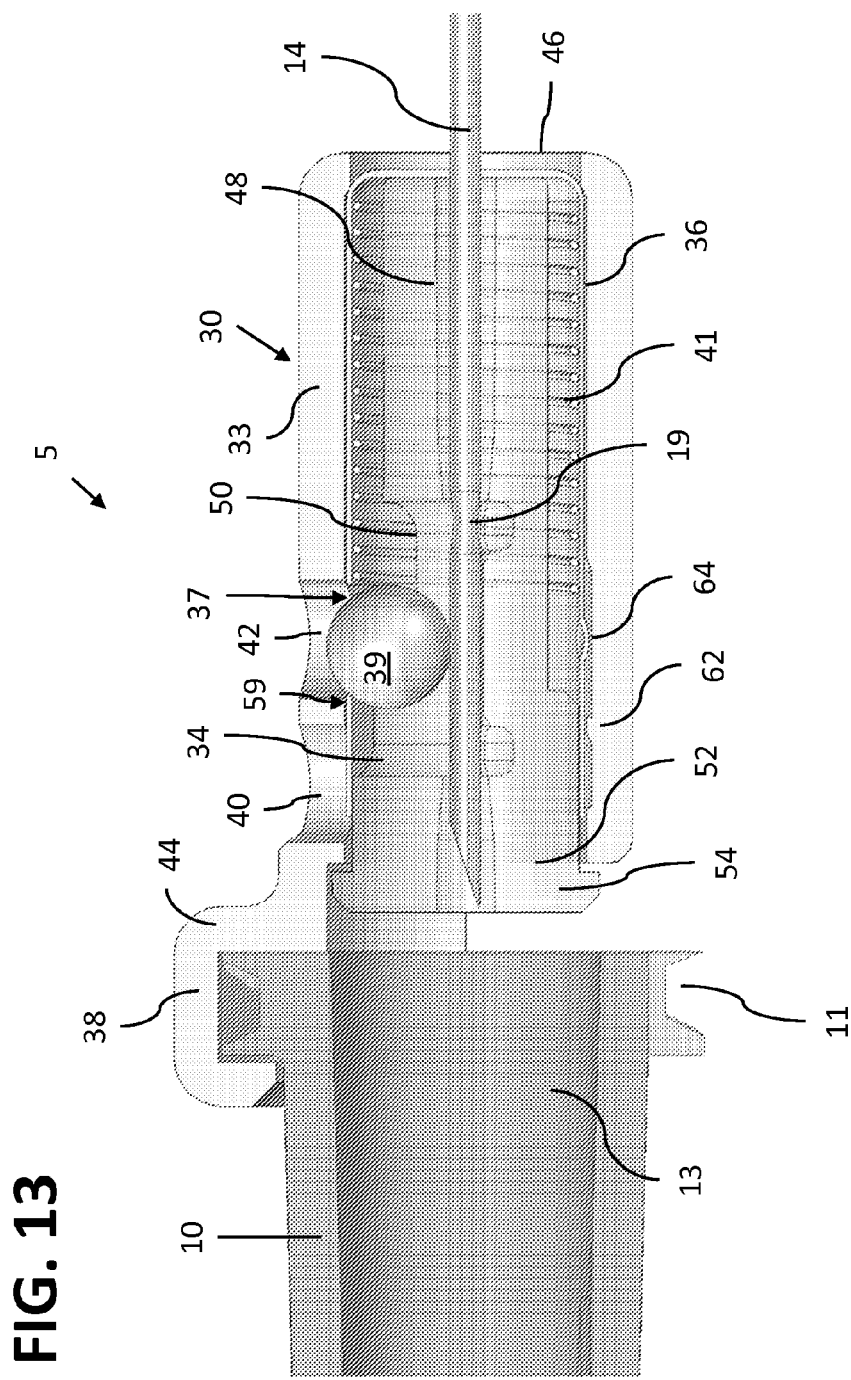
FIG. 13 shows a detailed cross-sectional view of the needle shield assembly in an intermediate step of manufacturing the device in accordance with embodiments of the invention.

With reference to FIG. 13, a needle blocking object 39 may be placed in carrier 34. Carrier 34 may include: a locking member 54 on, or engaged with, a distal end 52 thereof, and a channel 50 for carrying needle blocking object 39. Carrier 34 may be inserted into shroud 36 until a proximal end of carrier 34 abuts proximal end 56 of shroud 36. Shroud 36 is then inserted into latch 32 until proximal end 56 of shroud 36 abuts a reduced diameter portion at a proximal end of latch 32.

Latch 32 includes a latch member 38 extending from a portion of a distal end 44 of latch 32. Latch 32 further includes a first opening 40 through a wall thereof, and a second opening 42 through a wall thereof, located proximally of first opening 40.

Figure 14:
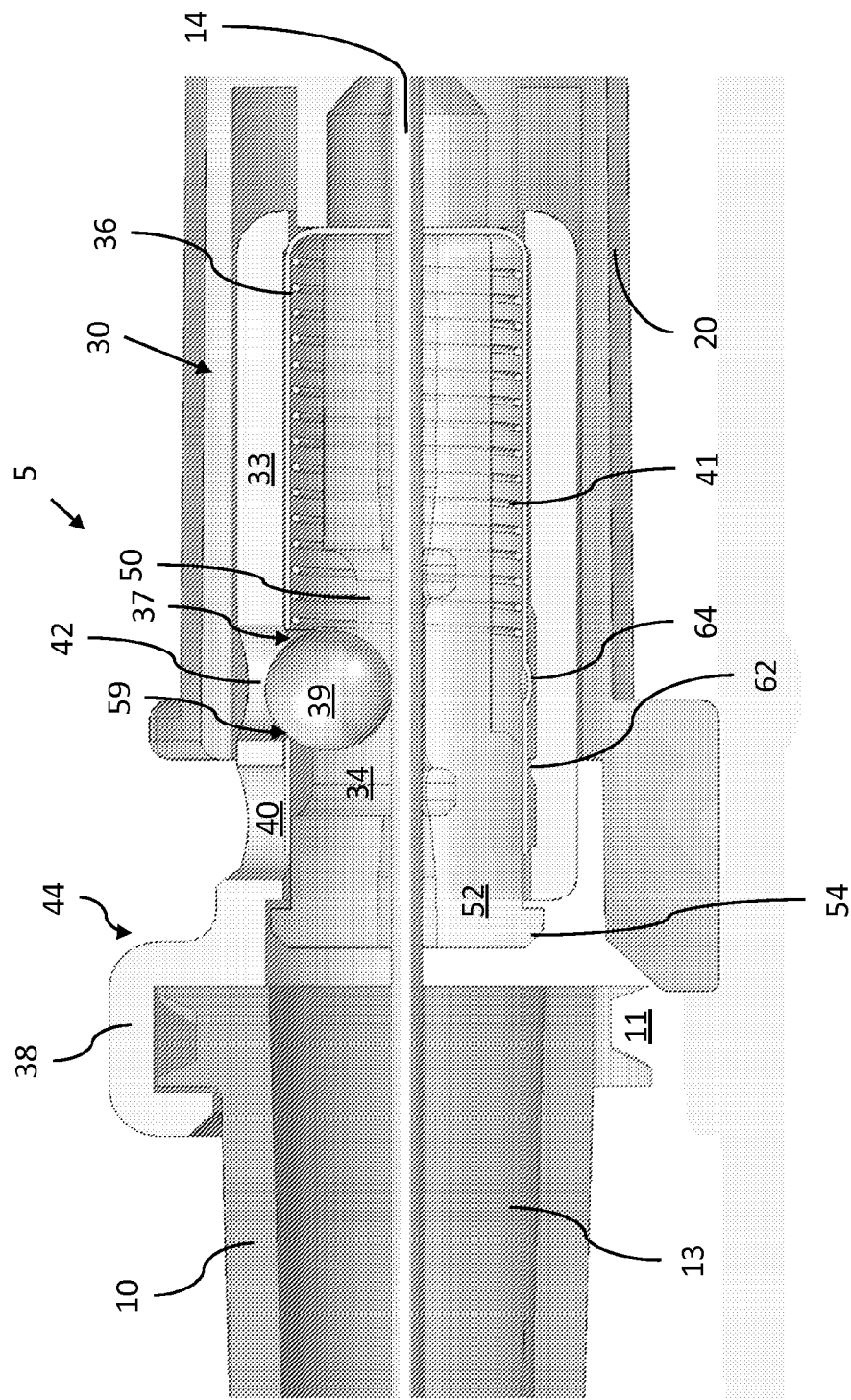
FIG. 14 shows a detailed cross-sectional view of the needle shield assembly and hub in an intermediate step of manufacturing the device in accordance with embodiments of the invention.
Figure 15:
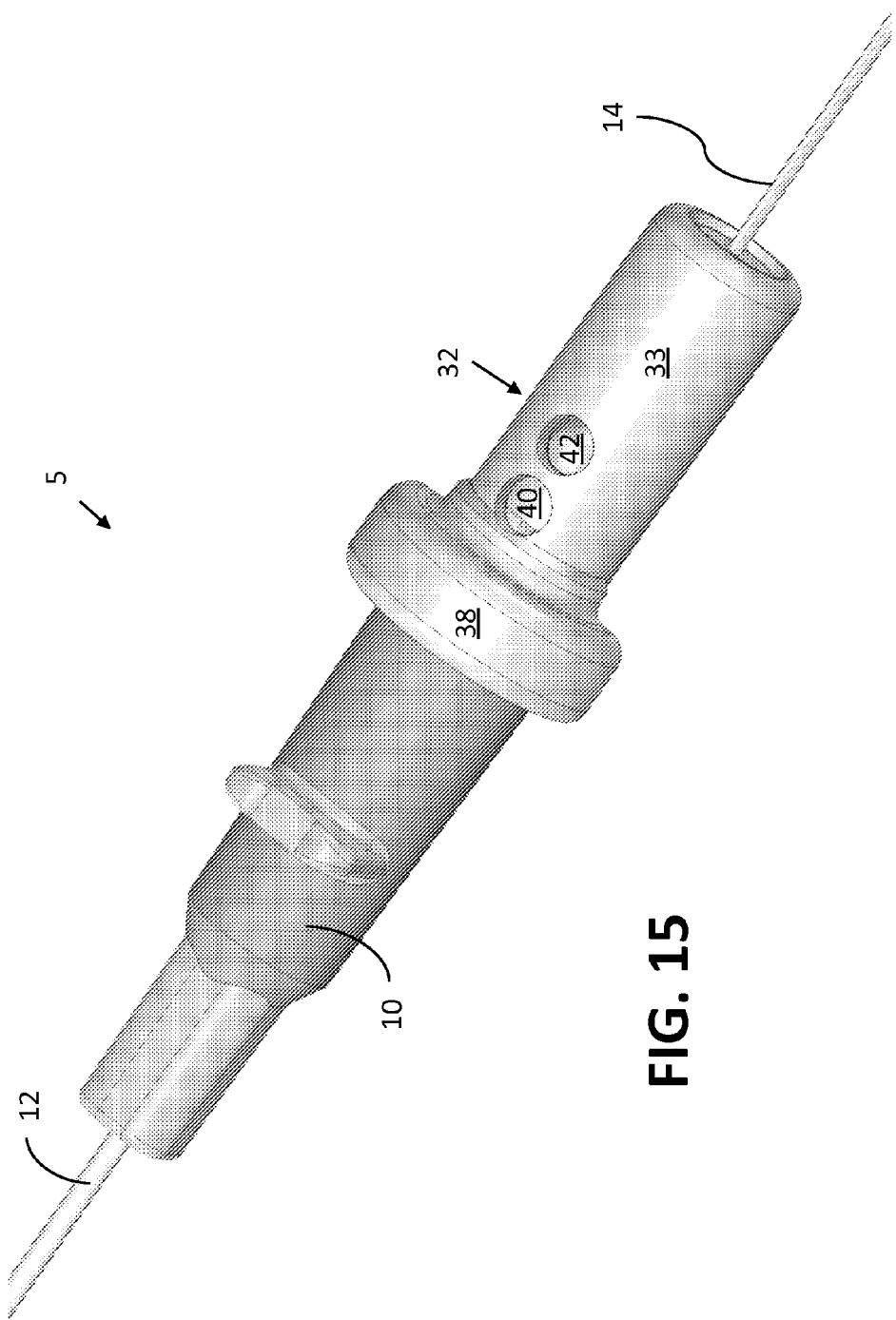
FIG. 15 shows a perspective view of a needle device including a needle shield assembly according to embodiments of the invention.

Proximal end 18 of needle 14 is inserted into distal end 52 of axial lumen 48 in carrier 34. Needle 14 displaces needle blocking object 39 such that it protrudes at least partially into second opening 42 in latch 32, as shown in FIG. 13. Proximal end 18 of needle 14 is then affixed to needle hub 20, for example, with glue as shown in FIGS. 3 and 5. Hub 10 may have a flanged proximal end 11. Latch member 38 is engaged with flanged proximal end 11 of hub 10 as shown in FIG. 14. Hub 10 and cannula 12 are then threaded over distal tip 16 of needle 14. Needle shield assemby 30 is then inserted into needle hub 20, causing boss 21 to push locking member 54 distally into hub 10, slip fitting closely into it as hown in FIG. 5.

Hub 10 may include a female luer adapter 13 therein. The foregoing engagement of latching member 38 with flanged proximal end 11 of hub 10, and the insertion of locking member 54 into hub 10 cause needle blocking object 39 to move distally within carrier 34 and out of second opening 42 (FIGS. 14-15), such that it protrudes into first opening 40 in latch 32 as in FIG. 5. Latch 32 may be configured to flex or expand slightly to allow needle blocking object 39 to snap from second opening 42 to first opening 40. Needle shield assembly 30 is thus locked onto hub 10 and is ready for deployment as described herein.

As used herein, the terms "first," "second," and the like, do not denote any order, quantity, or importance, but rather are used to distinguish one element from another, and the terms "a" and "an" herein do not denote a limitation of quantity, but rather denote the presence of at least one of the referenced item. The modifier "about" used in connection with a quantity is inclusive of the stated value and has the meaning dictated by the context (e.g., includes the degree of error associated with measurement of the particular quantity). The suffix "(s)" as used herein is intended to include both the singular and the plural of the term that it modifies, thereby including one or more of that term (e.g., the metal(s) includes one or more metals). Ranges disclosed herein are inclusive and independently combinable (e.g., ranges of "up to about 25 mm, or, more specifically, about 5 mm to about 20 mm," is inclusive of the endpoints and all intermediate values of the ranges of "about 5 mm to about 25 mm," etc.).

While various embodiments are described herein, it will be appreciated from the specification that various combinations of elements, variations or improvements therein may be made by those skilled in the art, and are within the scope of the invention. In addition, many modifications may be made to adapt a particular situation or material to the teachings of the invention without departing from essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A needle device comprising:
   a hub having a longitudinal axis;
   a needle having a sharp distal tip;
   a needle shield assembly associated with the needle and moveable from a non-shielding position to a shielding position in which the sharp distal tip is covered by at least part of the needle shield assembly;
   a latch engaging with a radially outer surface of the hub when the needle shield assembly is in the non-shielding position; and
   a locking member operably connected to the needle shield assembly, and located at least partially within the hub when the needle shield assembly is in the non-shielding position, thereby locking the latch to the hub, and such that when the needle shield assembly moves into the shielding position, the locking member moves generally proximally, thereby unlocking the latch.

2. The needle device of claim 1 wherein, when the needle shield assembly moves proximally out of the hub, the latch moves generally radially outward relative to the longitudinal axis.

3. The needle device of claim 2, wherein the latch comprises a housing coupled to a latch member.

4. The needle device of claim 3, wherein the housing includes a first opening extending through a wall thereof.

5. The needle device of claim 1, wherein the needle shield assembly comprises:
   a needle blocking object;
   a spring for biasing the needle blocking object distally and toward the longitudinal axis; and
   a carrier for carrying the needle blocking object.

6. The needle device of claim 5, wherein the carrier includes:
   a channel in which the needle blocking object is carried,
   an axial lumen slidable on and dimensioned to accommodate the needle, and
   an external shroud providing an opening through which a portion of the needle blocking object projects in the non-shielding position,
   wherein in the shielding position, the needle blocking object at least partially occupies the axial lumen.

7. The needle device of claim 5, wherein the locking member further comprises a flange coupled to a distal end of the carrier.

8. The needle device of claim 6, wherein the external shroud includes a hole axially aligned with the axial lumen and dimensioned to accommodate the needle,
   wherein the needle further includes a crimp having a larger outer diameter than that of the needle,
   wherein the hole engages the crimp to provide a stop preventing further proximal movement of the needle, and
   wherein the sharp distal tip of the needle is shielded by the needle shield assembly when the crimp engages the hole.

9. The needle device of claim 6, wherein the external shroud further comprises a substantially cylindrical member having an open distal end.

10. The needle device of claim 6, wherein the housing further comprises a first protrusion on an inner surface thereof, and the external shroud further comprises a second protrusion on an outer surface thereof,
    wherein the first protrusion interacts with the second protrusion as the needle shield assembly moves proximally from the non-shielding position to the shielding position, and wherein a pull-out force required to move the carrier proximally relative to the housing is greater than a frictional force between the needle blocking object and the needle.

11. The needle device of claim 1, wherein the hub comprises a flanged proximal end.

12. The needle device of claim 11, wherein the hub further comprises a threaded flanged proximal end.

13. The needle device of claim 3, wherein the latch member extends circumferentially between about 90° and about 180° about a distal end of the housing.

14. The needle device of claim 3, wherein the latch member comprises a hooked leg having:
   a first member extending radially outward relative to the housing,
   a second member extending distally from a radially outward end of the first member in a direction substantially parallel to the housing, and
   a third member extending radially inward from a distal end of the second member, forming a distal restraining surface of the latch,
   wherein an angle formed by the second member and the third member is about 135°.

15. The needle device of claim 14, wherein a first distance between a radially inward end of the third member and a distal end of the locking member is less than a second distance between a proximal-most point on an internal diameter of the hub and a distal-most point on an external diameter of a flange on a proximal end of the hub.

16. The needle device of claim 4, wherein the housing further includes a second opening extending through a wall thereof, located proximal of the first opening.

17. The needle device of claim 1, further comprising a needle hub disposed about the needle shield assembly, wherein the needle hub includes a boss abutting a proximal end of the needle shield assembly.

18. The needle device of claim 5, wherein in the non-shielding position,
   a portion of the needle blocking object protrudes into a first opening in the latch, and engages a proximal edge of the first opening.

19. The needle device of claim 18, wherein upon movement of the needle shield assembly from the non-shielding position to the shielding position,
   the needle blocking object exits the first opening in the latch under a force from the spring and at least partially enters the axial lumen to prevent emergence of the sharp distal end of the needle from the carrier.

20. The needle device of claim 1, wherein the hub further comprises a female luer adapter.

21. The needle device of claim 1, wherein the hub further comprises at least one of: a valve and a septum.

22. A needle device comprising:
   a hub comprising a luer connector with a luer thread and having a longitudinal axis;
   a needle having a sharp distal tip;
   a needle shield assembly associated with the needle and moveable from a non-shielding position to a shielding position in which the sharp distal tip is covered by at least part of the needle shield assembly;
   a latch engaging with the luer thread of the hub when the needle shield assembly is in the non-shielding position; and
   a locking member operably connected to the needle shield assembly and located at least partially in the luer connector when the needle shield assembly is in the non-shielding position, thereby locking the latch to the hub, and such that when the needle shield assembly moves into the shielding position, the locking member moves axially.

23. The needle device of claim 22, wherein the needle shield assembly comprises a needle blocking member adapted to move from a locking position in which the needle blocking member locks the needle shield assembly to the luer connector and maintains the locking member at least partially in the hub to the shielding position in which the needle blocking member releases the needle shield assembly from the luer connector and releases the locking member so that the locking member unlocks the latch and moves outwards relative to the hub.

24. A needle device comprising:
   a hub comprising a luer connector with a luer thread and having a longitudinal axis;
   a needle having a sharp distal tip; and
   a housing comprising:
   a needle shield assembly associated with the needle and operably connected to the housing, the needle shield assembly being moveable from the non-shielding position to a shielding position in which the sharp distal tip is covered by at least part of the needle shield assembly;
   a latch engaging with the luer connector of the hub when the needle shield assembly is in a non-shielding position; and
   the needle shield assembly further comprising a locking member located at least partially in the hub when the needle shield assembly is in the non-shielding position, thereby locking the latch to the luer connector, and such that when the needle shield assembly moves into the shielding position, the locking member moves axially thereby allowing the latch to move radially relative to the longitudinal axis.

25. The needle device of claim 24, wherein the needle shield assembly further comprises a needle blocking member adapted to move from a locking position in which the needle blocking member locks the needle shield assembly to the housing to a needle blocking position in which the needle blocking member releases the housing, thereby releasing the latch.

26. A method of manufacturing a needle assembly comprising:
   placing a blocking object in a carrier, wherein the carrier includes a flange disposed on a distal end thereof;
   inserting the carrier into a shroud;
   inserting the shroud into a housing until the proximal end of the shroud abuts a reduced diameter portion at a proximal end of the housing, wherein the housing includes a hooked member circumferentially extending from a portion of a distal end of the housing, and a first, distal opening and a second, proximal opening are provided through a wall of the housing;
   inserting a proximal end of a needle into an axial lumen of the carrier, thereby displacing the blocking object such that the blocking object protrudes at least partially through the proximal, second opening in the housing;
   affixing the proximal end of the needle to a needle hub;
   engaging the hooked member with a flanged proximal end of a hub;
   threading the hub and a cannula over a distal end of the needle;
   inserting the housing into the needle hub, wherein the engaging and inserting the housing causes the blocking object to move distally such that it protrudes from the first, distal opening in the housing.

* * * * *